United States Patent
Kim et al.

(10) Patent No.: US 9,541,561 B2
(45) Date of Patent: Jan. 10, 2017

(54) METHOD FOR DIAGNOSING ALZHEIMER'S DISEASE USING BIOMATERIAL

(71) Applicant: Electronics and Telecommunications Research Institute, Daejeon (KR)

(72) Inventors: Chang-Beom Kim, Seoul (KR); Kibong Song, Daejeon (KR); Kwan Su Kim, Seoul (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 148 days.

(21) Appl. No.: 13/843,574

(22) Filed: Mar. 15, 2013

(65) Prior Publication Data

US 2013/0337466 A1 Dec. 19, 2013

(30) Foreign Application Priority Data

Jun. 14, 2012 (KR) .................. 10-2012-0063853
Nov. 12, 2012 (KR) .................. 10-2012-0127613

(51) Int. Cl.
*G01N 33/543* (2006.01)
*G01N 33/68* (2006.01)

(52) U.S. Cl.
CPC ..... *G01N 33/6896* (2013.01); *G01N 33/54326* (2013.01); *G01N 33/54373* (2013.01)

(58) Field of Classification Search
None
See application file for complete search history.

(56) References Cited

U.S. PATENT DOCUMENTS

2004/0234417 A1* 11/2004 Schienle et al. ........... 422/82.08
2007/0047037 A1* 3/2007 Yoshizawa et al. ............. 359/3
2007/0057144 A1* 3/2007 Asano .......................... 250/200
(Continued)

FOREIGN PATENT DOCUMENTS

KR 10-2007-0073778 A 7/2007
KR 10-2009-0039864 A 4/2009
(Continued)

OTHER PUBLICATIONS

Daniel Johnstone et al., "Multivariate Protein Signatures of Pre-Clinical Alzheimer's Disease in the Alzheimer's Disease Neuroimaging Initiative (ADNI) Plasma Proteome Dataset", PLOS ONE, Apr. 2012, pp. 1-17, vol. 7, Issue 4.
(Continued)

*Primary Examiner* — Rebecca Martinez (57) ABSTRACT

Provided is a method for diagnosing Alzheimer/s disease using a decomposed biomaterial. The method includes: preparing magnetic particles on which primary capture antibodies specifically bound to beta-amyloid are adsorbed; decomposing a biomaterial including beta-amyloid; binding the beta-amyloid to the primary capture antibodies; binding secondary capture antibodies labeled with a fluorescent material to the magnetic particles bound to the beta-amyloid to form a complex; disposing the complex in a channel region of a photo field effect transistor in which a photocurrent is changed according to the amount of incident light; and measuring the photocurrent changed by light excited from the complex to quantify the concentration of the beta-amyloid existing in the biomaterial.

12 Claims, 12 Drawing Sheets

(56) References Cited

U.S. PATENT DOCUMENTS

| | | | |
|---|---|---|---|
| 2007/0231790 A1* | 10/2007 | Su | 435/5 |
| 2008/0063566 A1* | 3/2008 | Matsumoto | G01N 33/5438 |
| | | | 422/68.1 |
| 2009/0123459 A1 | 5/2009 | Jung et al. | |
| 2010/0144793 A1* | 6/2010 | Froestl et al. | 514/333 |
| 2010/0200781 A1* | 8/2010 | Khorasani et al. | 250/576 |
| 2010/0233734 A1* | 9/2010 | Hobbs | 435/7.24 |
| 2011/0020459 A1* | 1/2011 | Achrol | B01L 3/502753 |
| | | | 424/520 |

FOREIGN PATENT DOCUMENTS

| | | |
|---|---|---|
| KR | 10-2009-0048192 A | 5/2009 |
| KR | 10-2009-0098941 A | 9/2009 |
| KR | 10-2009-0110101 A | 10/2009 |
| KR | 10-2011-0112177 A | 10/2011 |
| KR | 10-2011-0119513 A | 11/2011 |

OTHER PUBLICATIONS

Jonathan M. Schott et al., "Increased Brain Atrophy Rates in Cognitively Normal Older Adults with Low Cerebrospinal Fluid Aβ1-42", Annals of Neurology, 2010, pp. 825-834, vol. 68, No. 6, American Neurological Association.

* cited by examiner

METHOD FOR DIAGNOSING ALZHEIMER'S DISEASE USING BIOMATERIAL

CROSS-REFERENCE TO RELATED APPLICATIONS

This U.S. non-provisional patent application claims priority under 35 U.S.C. §119 of Korean Patent Application No. 10-2012-0063853, filed on Jun. 14, 2012 and No. 10-2012-0127613, filed on Nov. 12, 2012 the entire contents of which are hereby incorporated by reference.

BACKGROUND OF THE INVENTION

The present invention disclosed herein relates to methods for diagnosing Alzheimer's disease, and more particularly, to methods for diagnosing Alzheimer's disease using a biomaterial.

As the average length of life increases globally in these days and the society structure enters the aging society, Alzheimer's disease that is the most common form of dementia, i.e., senile neurodegenerative disease, has drastically come to the fore as social-economic and medical issue. While the current medical techniques fail to treat Alzheimer's disease or stop pathologic progress, it is possible to alleviate the progression speed of Alzheimer's disease and thus treatment is focused on such alleviation. Up to the now since the early 1900s when this disease was found, studies on Alzheimer's disease have been performed in various fields such as biology, biochemistry, cognitive ethology, etc., and importance of early diagnosis of Alzheimer's disease begins to emerge in recent years. Early diagnosis and caring of Alzheimer's disease is the best way able to decrease psychological and financial burden and to improve the quality of life in terms of a social-economical aspect as well as a personal aspect.

An existing diagnosis of Alzheimer's disease depends on time-consumptive and complex evaluation methods, such as a clinical evaluation, psychological testing, brain imaging, discrimination from other neurodegenerative diseases, etc. In this regards, detection of a molecular level biomarker that may confirm the diagnosis of Alzheimer's disease, discriminate the pathological severity degree in patients, expect the progression rate of a disease in patients, and monitor the progression state is the most useful way. Such a molecular-level biomarker should have a neuropathological basic characteristic, and sensitivity and specificity that are second to the clinical diagnosis level. Also, the molecular-level biomarker may be said to be ideal when it has reliability and reproducibility and a sample including the biomarker therein is extracted while accompanying low cost, noninvasion and easiness. Examples of existing Alzheimer's disease-related samples may include skin tissue, rectum tissue, bone-marrow, spinal fluid, etc., and collection of these samples may be said to be unsuitable for regular clinical diagnosis.

For example, a brain imaging technique using a high resolution brain imaging apparatus is an existing diagnosis method of Alzheimer's disease. The early diagnosis method of Alzheimer's disease using the brain imaging technique studies the preciseness of the brain imaging apparatus by scanning the brain of a suspected Alzheimer's disease patient to measure abnormal accumulation of beta-amyloid protein and comparing and analyzing the measured results with autopsy results of brain tissue after death. However, since this image-based diagnosis method requires a patient to pay high cost and discrimination is performed in a state that brain contraction or damage is progressed, detection of a disease is late. Another representative diagnosis method is a diagnosis of spinal fluid and measures a change in amount of beta-amyloid protein in the brain and spinal cord. However, the inspection method of the brain and spinal cord itself is known to be a very painful method, and is blamed for dangerousness accompanied during the inspection.

SUMMARY OF THE INVENTION

The present invention provides methods for diagnosing Alzheimer's disease using a biomaterial.

The objects of the present invention are not limited to the foregoing those, and other objects will be clearly understood to those skilled in the art from the following description.

Embodiments of the present invention provide methods for diagnosing Alzheimer' disease include: preparing magnetic particles on which primary capture antibodies specifically bound to beta-amyloid are adsorbed; decomposing a biomaterial including beta-amyloid; binding the beta-amyloid to the primary capture antibodies; binding secondary capture antibodies labeled with a fluorescent material to the magnetic particles bound to the beta-amyloid to form a complex; disposing the complex in a channel region of a photo field effect transistor in which a photocurrent is changed according to the amount of incident light; and measuring the photocurrent changed by light excited from the complex to quantify the concentration of the beta-amyloid existing in the biomaterial.

In some embodiments, the photo field effect transistor may include a light filter layer that passes through only a wavelength of light excited from the fluorescent material. The light filter layer may be a selenium (Se) thin layer.

In other embodiments, the photo field effect transistor may include a semiconductor substrate, an insulating layer on the semiconductor substrate, a channel pattern on the insulating layer, and wiring electrodes disposed spaced apart from each other on the channel pattern. The light filter layer may be disposed on the channel pattern.

In still other embodiments, the fluorescent material may be formed of a material emitting light of a wavelength band ranging from about 650 nm to about 850 nm by excitation beam of a wavelength band ranging from of about 400 nm to about 550 nm.

In even other embodiments, the biomaterial may be at least one of spinal fluid, blood and olfactory cell.

In other embodiments of the present invention, methods for diagnosing Alzheimer's disease include: preparing comparative samples having different concentrations of beta-amyloid from each other; preparing sampling magnetic particles in which the beta-amyloid existing in each of the comparative samples is bound to multiprotein; measuring a change in photocurrent of the sampling magnetic particles by using a photo field effect transistor in which a photocurrent is changed according to the amount of light, to thus generate reference data; decomposing a biomaterial including beta-amyloid; preparing magnetic particles in which the beta-amyloid is bound to the multiprotein; measuring a change in photocurrent of the magnetic particles by using the photo field effect transistor to generate a measurement data; and comparing the measured data with the reference data to determine Alzheimer's disease.

Specific items of other embodiments are included in the detailed description and drawings of the present invention.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF PREFERRED EMBODIMENTS

Preferred embodiments of the invention will be described below in more detail with reference to the accompanying drawings. The invention may, however, be embodied in many different forms and should not be construed as being limited to the embodiments set forth herein; rather, these embodiments are provided so that this disclosure will be thorough and complete, and will fully convey the concept of the invention to those skilled in the art. Further, the present invention is only defined by scopes of claims. Like reference numerals refer to like elements throughout.

In the following description, the technical terms are used only for explaining a specific exemplary embodiment while not limiting the present invention.

The terms of a singular form may include plural forms unless otherwise specified. Also, the meaning of "include," "comprise," "including," or "comprising," specifies a property, a region, a fixed number, a step, a process, an element and/or a component but does not exclude other properties, regions, fixed numbers, steps, processes, elements and/or components.

Description regarding methods for diagnosing Alzheimer's disease using a biomaterial according to embodiments of the present invention will be given in detail with reference to the accompanying drawings.

Figure 1A:
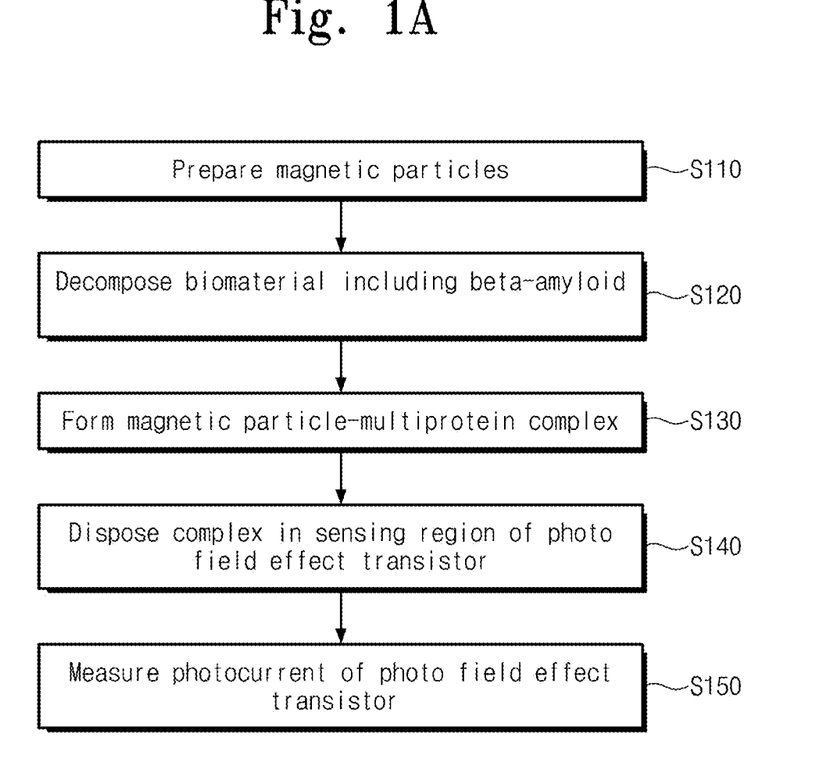
FIGS. 1A and 1B are flow diagrams a method of diagnosing Alzheimer's disease according to an embodiment of the present invention.
Figure 1B:
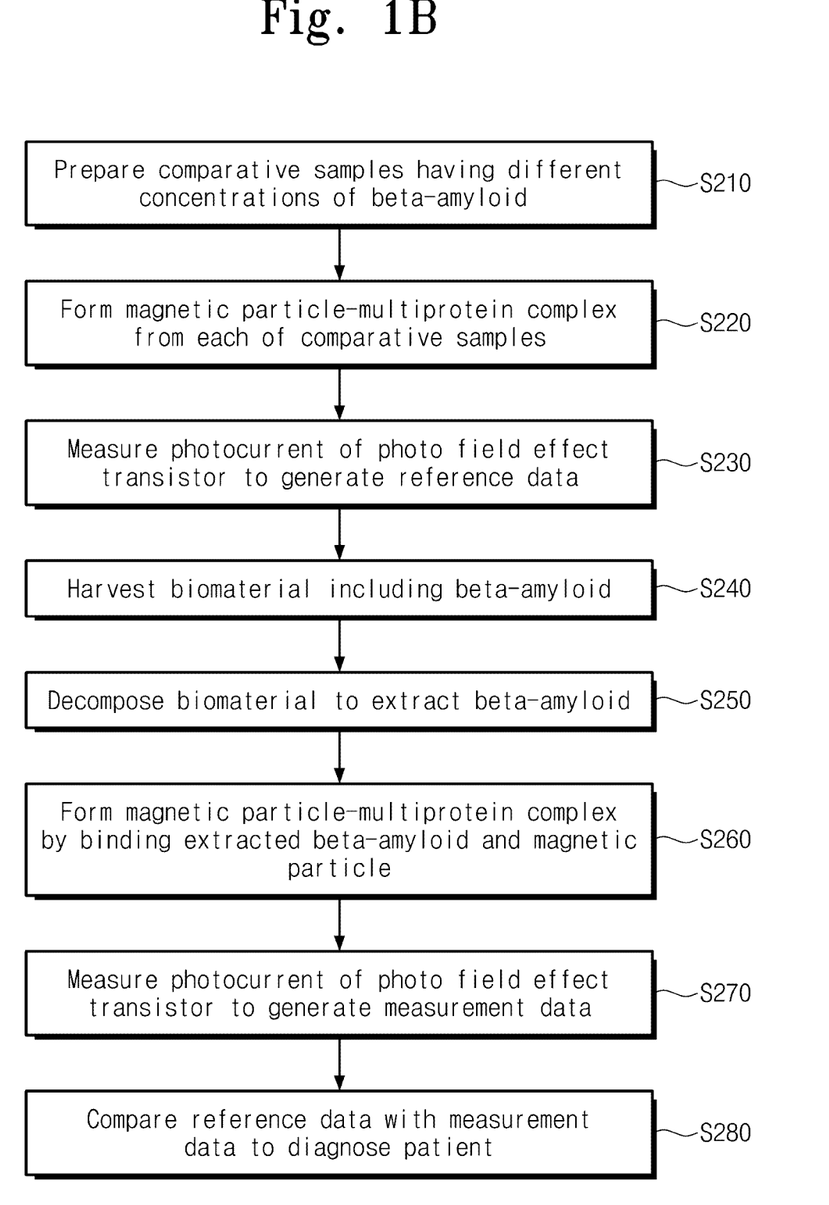

FIGS. 1A and 1B are flow diagrams a method for diagnosing Alzheimer's disease according to an embodiment of the present invention.

Referring to FIG. 1A, magnetic particles for diagnosis of Alzheimer's disease are prepared (S110). A primary capture antibody which is selectively bound to beta-amyloid protein that is the cause of Alzheimer's disease among many proteins existing in the biomaterial may be adsorbed to surfaces of the magnetic particles.

The biomaterial including beta-amyloid protein is decomposed using a lysis solution or the like (S120). Then, beta-amyloid is extracted.

The magnetic particles to which beta-amyloid is bound are labeled with a fluorescent body to form a magnetic particle-multiprotein complex (S130). To quantify the concentration of beta-amyloid using a photo field effect transistor, the magnetic particles to which beta-amyloid is bound may be labeled with a fluorescent body.

The magnetic particle-multiprotein complex is disposed in a channel region of the photo field effect transistor (S140). The magnetic particle-multiprotein complex may be fixed in the channel region of the photo field effect transistor by using an external magnetic field.

A photocurrent is measured in the photo field effect transistor to diagnose Alzheimer's disease and determine the severity degree of Alzheimer's disease (S150). When excitation beam is irradiated to the magnetic particle-multiprotein complex, the photocurrent of the photo field effect transistor may be changed by light emitted from the fluorescent material. Since the intensity of the emitted light is changed according to the amount of beta-amyloid bound to the magnetic particles, diagnosis of Alzheimer's disease and severity degree of Alzheimer's disease may be determined by measuring the change of the photocurrent.

Thus, in order to quantify the amount of beta-amyloid existing in the biomaterial and to determine diagnosis and severity degree of Alzheimer's disease, a reference data obtained by measuring the change in photocurrent according to the concentration of beta-amyloid may be prepared in advance.

In detail, referring to FIG. 1B, two or more comparative samples having different concentrations of beta-amyloid are prepared (S210), and then magnetic particles are added to each of the comparative samples to form a magnetic particle-multiprotein complex (S220). A change in photocurrent of the magnetic particle-multiprotein complexes obtained from the respective comparative samples is measured to generate a reference data (S230). For example, a first sample solution (i.e., an ordinary person) including beta-amyloid having a concentration range of about 1-10 pg/mg is prepared, a magnetic particle-multiprotein complex is formed, and the photocurrent of the formed magnetic particle-multiprotein complex is measured. As a result, a first reference data may be generated. Also, a second sample solution (i.e., an Alzheimer's disease patient) including beta-amyloid having a concentration range of about 15-5,000 pg/mg is prepared, a magnetic particle-multiprotein complex is formed, and the photocurrent of the formed magnetic particle-multiprotein complex is measured. As a result, a second reference data may be generated.

Thereafter, a biomaterial of a patient intended to diagnose Alzheimer's disease is harvested (S240). The biomaterial includes beta-amyloid. The biomaterial may be harvested from all kinds of living body tissues, preferably be at least one of spinal fluid, blood and olfactory cell, and more preferably be olfactory cell. The olfactory sense of the Alzheimer's disease patient may be weakened. An olfactory cell in a nose of a patient (or a suspected Alzheimer's disease person) may be harvested. The olfactory cell may be harvested immediately from a patient without a separate culture process, and then decomposed and used. The biomaterial is decomposed using a lysis solution to extract beta-amyloid (S250).

As explained with reference to FIG. 1A, a complex in which beta-amyloid extracted from the decomposed biomaterial and the magnetic particles are bound is formed (S260). Thereafter, a change in photocurrent of the complex obtained from a diagnosis subject is measured using a photo field effect transistor to generate a measurement data (S270). Next, the measurement data may be compared with the first reference data and the second reference data to thus diagnose Alzheimer's disease of the subject (S280).

Also, various sample solutions including beta-amyloid having a concentration range of about 15-5,000 pg/ml are prepared to generate two or more reference data, the concentrations of beta-amyloid existing in the biomaterials are quantified, and the reference data and the quantified data are compared to finely grade the severity degree of Alzheimer's disease.

Figure 1C:
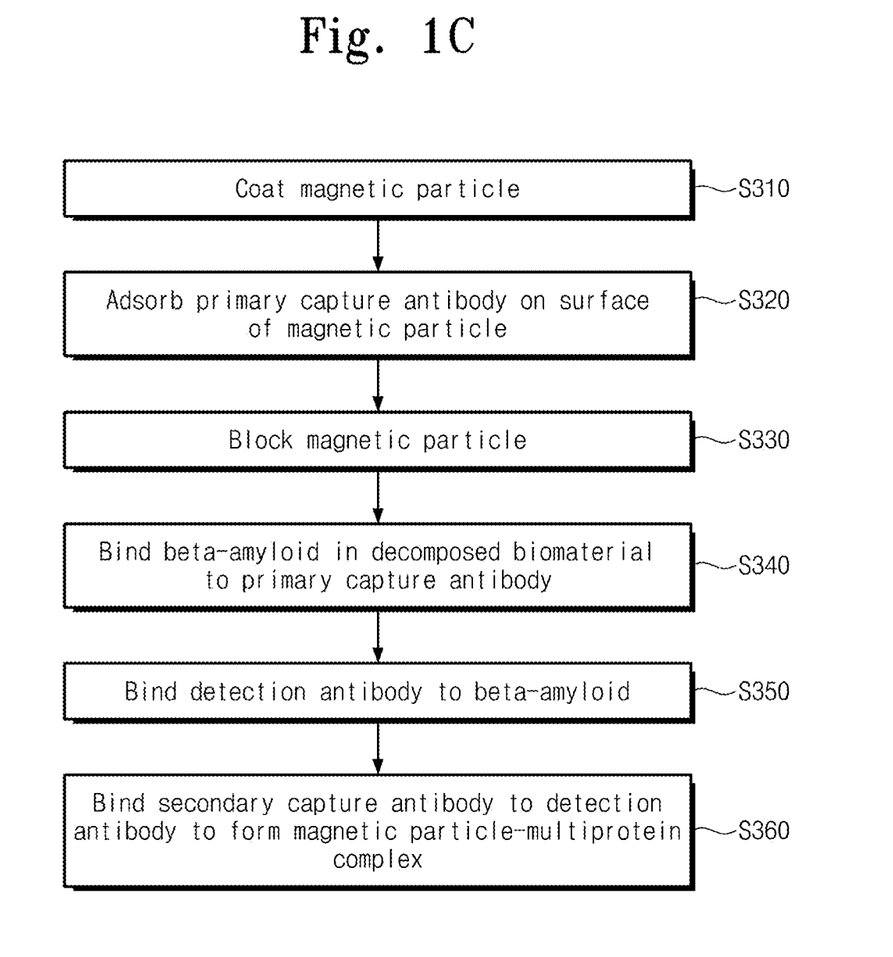
FIG. 1C is a flow diagram illustrating a method of forming a magnetic particle-multiprotein complex according to an embodiment of the present invention.

FIG. 1C is a flow diagram illustrating a method of forming a magnetic particle-multiprotein complex according to an embodiment of the present invention. FIGS. 2A through 2E are schematic views illustrating a method of forming the magnetic particle-multi-protein complex.

According to embodiments, a magnetic particle (10)-multiprotein complex 100 in which beta-amyloid is bound to a surface of the magnetic particle 10 may be formed by an antigen-antibody reaction.

Figure 2A:
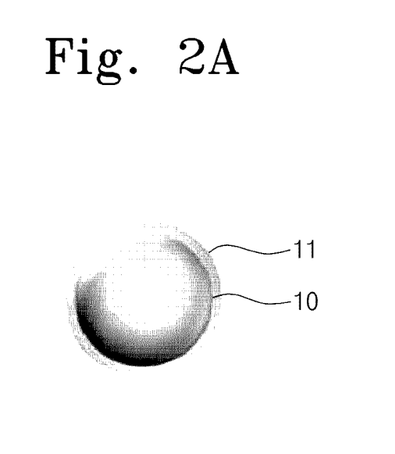
FIGS. 2A through 2E are schematic views illustrating a method of forming the magnetic particle-multiprotein complex.

Referring to FIGS. 1C and 2A, the magnetic particle 10 for diagnosis of Alzheimer's disease is prepared. The magnetic particle 10 may be a fine particle having a diameter ranging from about 100 nm to about 5 μm. The magnetic particle 10 may include any one of Fe, Mn, Ni and Co. For example, the magnetic particle 10 may be composed of Fe, ε-Co, Co, Ni, FePt, CoPt, γ-$Fe_2O_3$, $Fe_3O_4$, CoO, $CoFe_2O_4$, or the like.

The magnetic particle 10 may have a surface which is functionalized so as to uniformly adsorb a primary capture antibody 12 selectively bound only to beta-amyloid. For example, a functional group, such as carboxyl group (—COOH), a thiol group (—SH), a hydroxyl group (—OH), a silane group, an amine group (—$NH_2$) or an epoxy group may be induced to the surface of the magnetic particle 10.

The surface of the magnetic particle 10 is coated (or pre-treated) such that the primary capture antibody 12 may be adsorbed to the surface of the magnetic particle 10 with a uniform distribution (S310). The coating (or pre-treating) of the surface of the magnetic particle 10 is performed by reacting the magnetic particle 10 with EDC (1-ethyl-3-(3-dimethylaminopropyl)carbodiimide) or CMC (1-cyclohexyl-3(2-morpholinoethyl)carbodiimide metho-p toluensulfonate), so that a coating film 11 is formed.

Figure 2B:
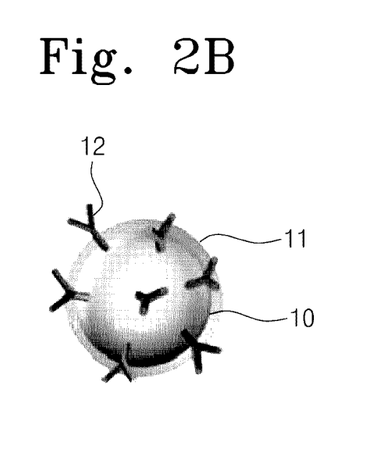

Referring to FIGS. 1C and 2B, the primary capture antibody 12 selectively bound only to beta-amyloid that is the cause of Alzheimer's disease (or a biomarker causing Alzheimer's disease) is adsorbed to the surface of the magnetic particle 10 (S320).

After the primary capture antibody 12 is adsorbed to the surface of the pre-treated magnetic particle 10, the resultant magnetic particle is cultured for two hours at room temperature. At this time, by using a monoclonal antibody, the specificity of the primary capture antibody 12 selectively bound only to beta-amyloid protein may be enhanced.

Referring to FIG. 1C, after culturing, the magnetic particle 10 is blocked in order to prevent other proteins from being nonspecifically bound to the surface of the magnetic particle 10 that is not bound to the primary capture antibody 12 (S330). That is, a blocking material may be adsorbed to the surface of the magnetic particle 10. For example, goat-serum or 1-4% bovine serum albumin (BSA) may be used as the blocking material, and after the blocking material is adsorbed, the resultant magnetic particle is cultured for two hours at room temperature.

Figure 2C:
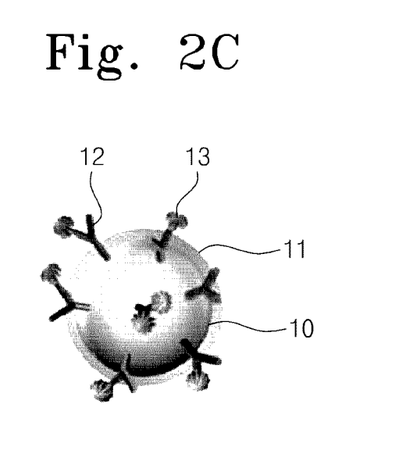

Referring to FIGS. 1C and 2C, beta-amyloid 13 corresponding to an antigen extracted from the decomposed biomaterial is fixed to the magnetic particle 10. (S340)

Figure 2D:
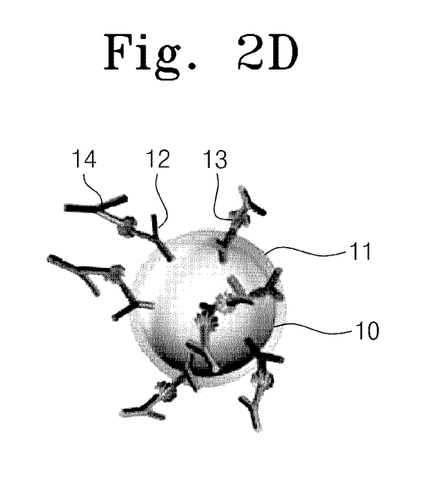

Referring to FIGS. 1C and 2D, a detection antibody 14 is bound to the beta-amyloid 13 bound to the primary capture antibody 12 (S350). In detail, a reaction is performed for two hours such that the detection antibody 14 is bound to other epitopes of the beta-amyloid 13 bound to the primary capture antibody 12. At this time, when a polyclonal antibody is used as the detection antibody 14, the binding probability between the detection antibody 14 and the beta-amyloid may be increased. An antibody produced from a host animal that is different from the host animal of the primary capture antibody 12 may be used as the detection body 14. The type of the host animal from which the detection antibody 14 is produced is selected to be the same as that of the serum antigen of a secondary capture antibody 15 in a next stage.

Figure 2E:
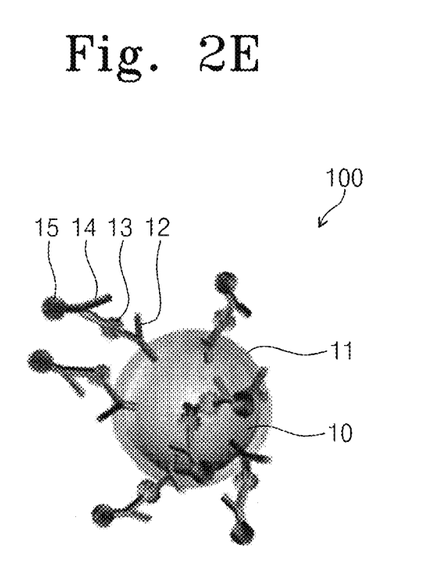

Referring to FIGS. 1C and 2E, the secondary capture antibody 15 which is bound only to the detection antibody 14 bound to the beta-amyloid 13 is bound to the detection antibody 14 to form a magnetic particle-multiprotein complex 100 (S360).

To quantitatively grasp the amount of beta-amyloid bound to the magnetic particle 10, the secondary capture antibody 15 may be labeled with a fluorescent body. The secondary capture antibody 15 is specifically bound only to the detection antibody 14 but is not specifically bound to the primary capture antibody 12.

The secondary capture antibody 15 may be labeled with a fluorescent body before being provided to the magnetic particle 10 to which the beta-amyloid is bound. The fluorescent body may be selected from materials emitting light of a wavelength band passing through a light filter layer included in the photo field effect transistor. For example, the fluorescent body may be formed of a material emitting light of a wavelength band ranging from about 650 nm to about 850 nm by excitation light of a wavelength band ranging from about 400 nm to about 550 nm.

Figure 3:
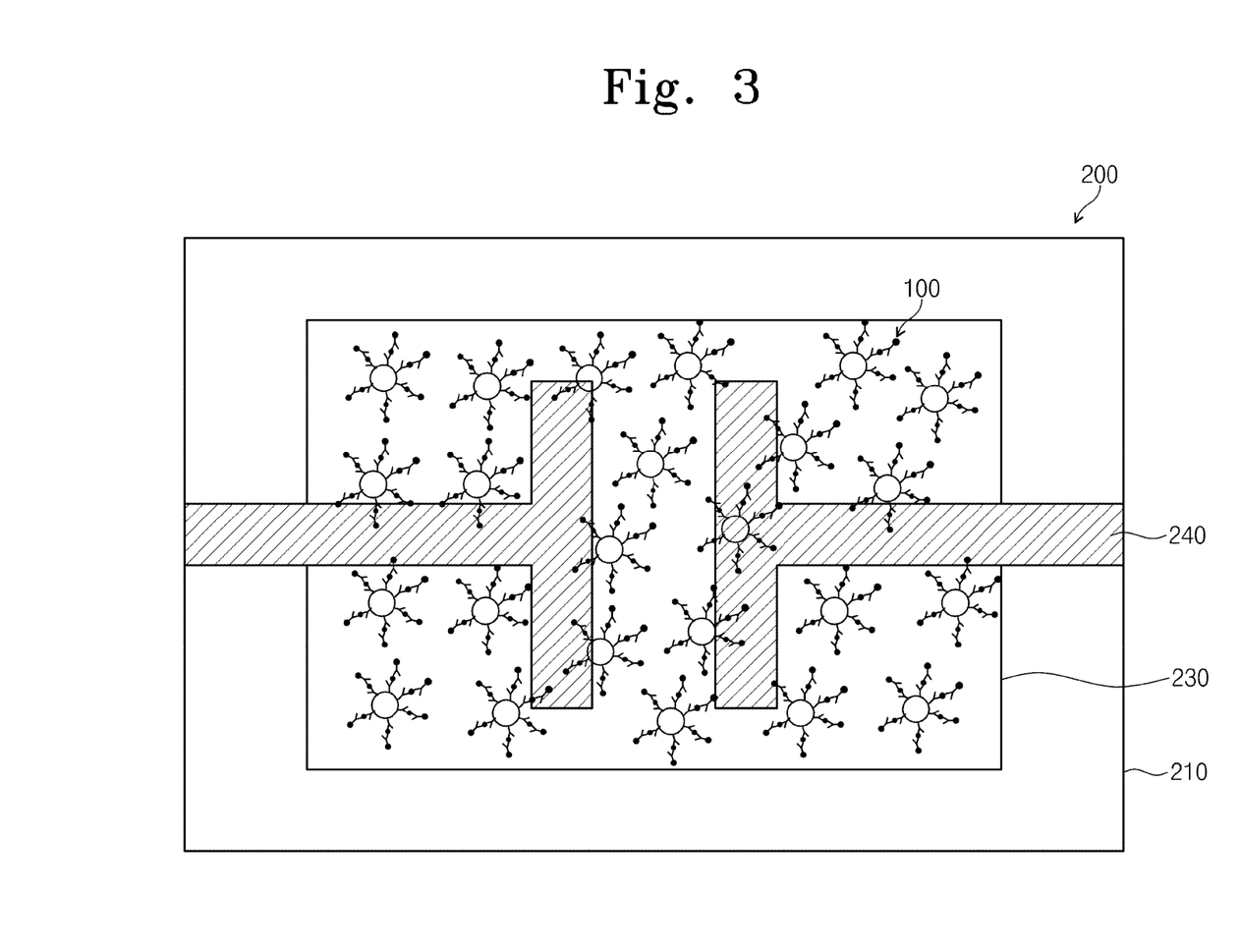
FIG. 3 is a schematic view illustrating a photo field effect transistor for diagnosis of Alzheimer's disease according to an embodiment of the present invention.
Figure 4:
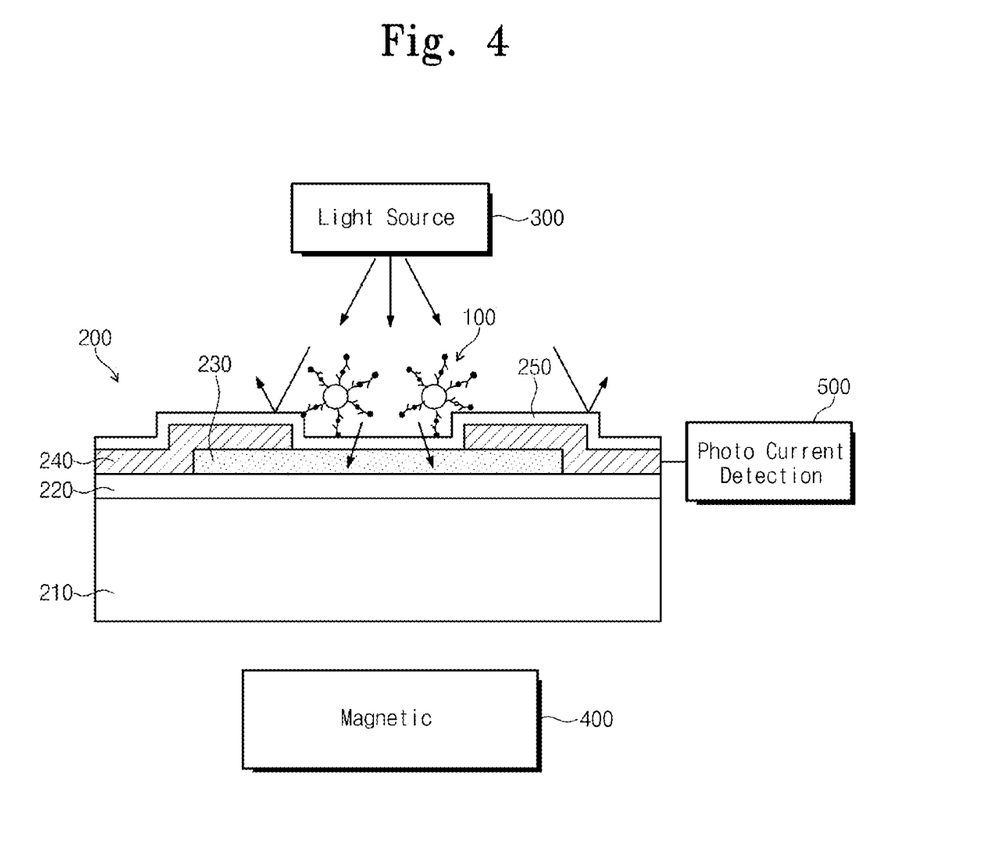
FIG. 4 is a schematic view illustrating an apparatus for detection of a biomaterial for diagnosis of Alzheimer's disease according to an embodiment of the present invention.

FIG. 3 is a schematic view illustrating a photo field effect transistor for diagnosis of Alzheimer's disease according to an embodiment of the present invention. FIG. 4 is a schematic view illustrating an apparatus for detection of a biomaterial for diagnosis of Alzheimer's disease according to an embodiment of the present invention.

Referring to FIGS. 3 and 4, a biomaterial detection apparatus includes a photo field effect transistor 200, a light source 300, a magnetic field generating unit 400, and a photocurrent meter 500. The photo field effect transistor 200 includes a semiconductor substrate 210, a channel pattern 230, wiring electrodes 240, and a light filter layer 250. The photo field effect transistor 200 may have a back-gate structure.

In detail, an insulating layer 220 is disposed on the semiconductor substrate 210, and the channel pattern 230 is disposed on the insulating layer 220. The insulating layer 220 may be a silicon oxide layer, a silicon oxynitride layer or a silicon nitride layer. The channel pattern 230 may be formed by depositing a semiconductor material and patterning the deposited semiconductor material. The channel pattern 230 may be made of amorphous silicon. The channel pattern 230 may be a micro fluidic channel.

The wiring electrodes 240 may be disposed spaced apart from each other on the channel pattern 230. The wiring electrodes 240 may be formed by depositing a conductive layer and patterning the deposited conductive layer. The wiring electrodes 240 may be electrically connected to the photocurrent meter 500 of the biomaterial detection apparatus to measure an electrical change in the channel pattern 230.

The light filter layer 250 is formed on the channel pattern 230 and wiring electrodes 240. The light filter layer 250 may be made of a light medium that reflects light of a specific wavelength band but passes through light of another specific wavelength band. According to an embodiment, the light filter layer 250 may be made of selenium (Se). As described with reference to FIGS. 2A through 2E, while the complexes 100 for diagnosis of Alzheimer's disease according to the embodiments of the present invention are formed, the secondary antibody may be determined according to the light transmission characteristic of the light filter layer 250. The light transmission characteristic of the light filter layer 250 made of selenium will be described with reference to FIGS. 5 and 6.

The magnetic particle-multiprotein complexes 100 may be disposed on the light filter layer 250 between the wiring electrodes 240. The magnetic particle-multiprotein complexes 100 may be fixed on the channel pattern 230 of the photo field effect transistor 200 by an external magnetic field 400 provided from a place under the semiconductor substrate 210. For example, a small sized magnet or a magnetic field generating unit may be disposed under the semiconductor substrate 210.

The complexes 100 are disposed on the light filter layer 250 and light is irradiated to the complexes 100 from the light source 300. Fluorescent light may be excited from the fluorescent bodies of the complexes 100 by incident light. At this time, the incident light provided from the light source 300 may be light of a specific wavelength band, and the fluorescent light emitted from the fluorescent body by incident light may pass through the light filter layer 250.

According to an embodiment, light of a wavelength band ranging from about 650 nm to about 850 nm may be emitted from the fluorescent bodies of the magnetic particle-multiprotein complexes 100 by excitation beam of a wavelength band ranging from about 400 nm to about 550 nm. The fluorescent light emitted from the fluorescent bodies may pass through the light filter layer 250 of the photo field effect transistor to change the photocurrent flowing through the channel pattern 230.

Figure 5:
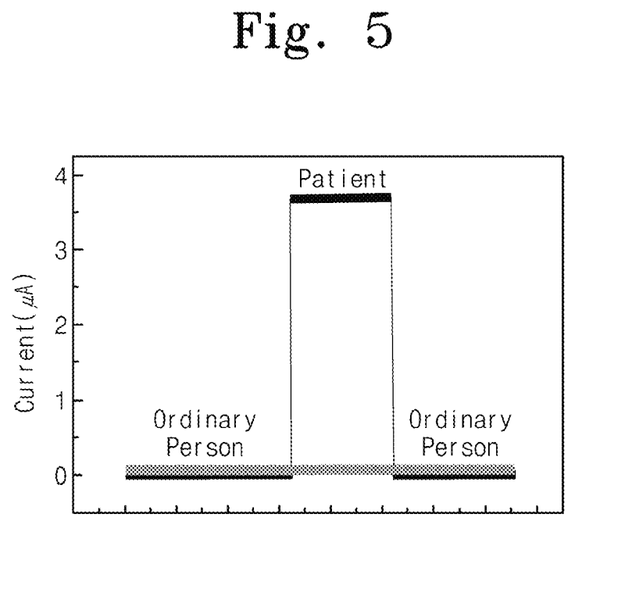
FIG. 5 is a graph illustrating a light characteristic condition in a photo field effect transistor for diagnosis of Alzheimer's disease according to an embodiment of the present invention.

FIG. 5 is a graph illustrating a light characteristic condition in a photo field effect transistor for diagnosis of Alzheimer's disease according to an embodiment of the present invention.

Figure 6:
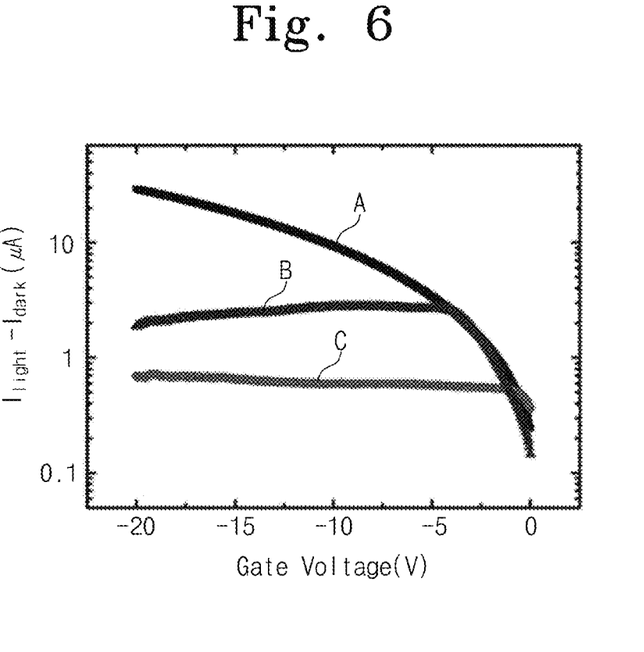
FIG. 6 is a graph illustrating a photocurrent characteristic in a photo field effect transistor for diagnosis of Alzheimer's disease according to an embodiment of the present invention.

FIG. 5 illustrates the light transmission characteristic of the light filter layer made of a selenium layer of the photo field effect transistor. Referring to FIG. 6, it may be seen that the light filter layer does not pass through light of a wavelength band of not more than about 600 nm but passes through only light of a wavelength band of about 650 nm.

Therefore, for diagnosis of Alzheimer's disease according to an embodiment of the present invention, the wavelength band of the excitation beam is set to about 540 nm and a secondary antibody emitting light of a wavelength of about 655 nm may be used.

FIG. 6 is a graph illustrating a photocurrent characteristic in a photo field effect transistor for diagnosis of Alzheimer's disease according to an embodiment of the present invention.

Graph 'A' of FIG. 6 illustrates a current generated from the photo field effect transistor by excitation beam (wavelength: 640 nm) in the case where the photo field effect transistor dose not have a light filter layer. Graph 'C' of FIG. 6 illustrates a current generation rate when a selenium thin layer is used as a light filter layer and excitation beam (i.e., light of a wavelength band of not more than about 600 nm) is filtered. When graph 'A' is compared with graph 'C', it may be confirmed that the current generation rate in the case of the photo field effect transistor having a light filter layer is lower than that in the case of the photo field effect transistor no having a light filter layer. Graph 'B' of FIG. 6 illustrates a current generation rate measured in a photo field effect transistor in the case where a magnetic particle-multiprotein complex exists on a selenium thin layer that is a light filter layer. Referring to Graph 'B', a current is generated by light (wavelength: 665 nm) emitted from the fluorescent body, and it may be confirmed that the generated current is smaller than the current generated when a photo field effect transistor does not have a selenium thin layer and is larger than the current generated when a photo effect field transistor has a selenium thin layer.

Figure 7:
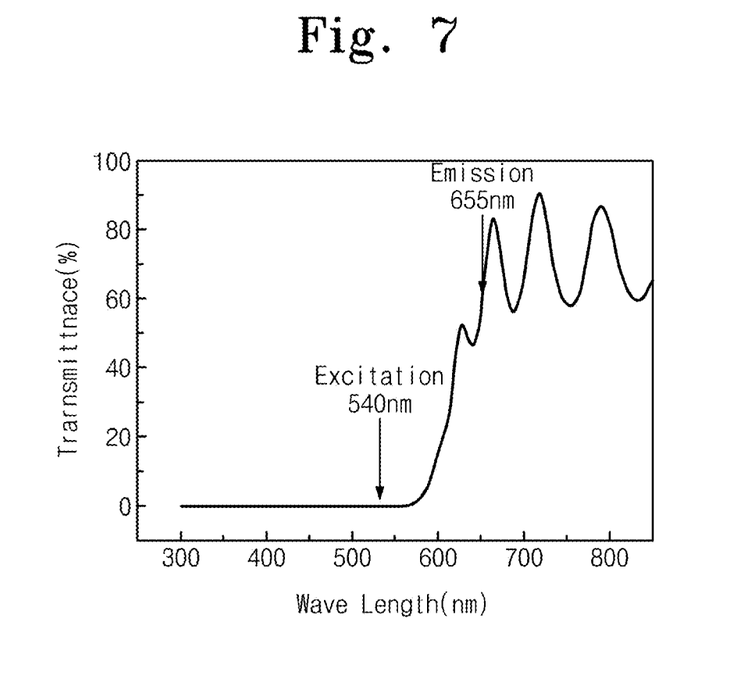
FIG. 7 is a graph illustrating a photocurrent characteristic according to the concentration of beta-amyloid existing in a biomaterial in a method for diagnosis of Alzheimer's disease according to an embodiment of the present invention.

FIG. 7 is a graph illustrating a photocurrent characteristic according to the concentration of beta-amyloid existing in a biomaterial in a method for diagnosis of Alzheimer's disease according to an embodiment of the present invention.

Referring to FIG. 7, in the case where a fine amount of beta-amyloid exists in a biomaterial (i.e., an ordinary person), since the beta-amyloid is not almost bound to the magnetic particle, the amount of light emitted from the complex of the photo field effect transistor is small. Accordingly, since the light passing through the light filter layer is small, it may be confirmed that the photocurrent measured in the photo field effect transistor is close to zero.

Unlike this, in the case where a large amount of beta-amyloid exists in the biomaterial (i.e., an Alzheimer's disease patient), since the amount of the beta-amyloid bound to the magnetic particle is large, the light emitted from the complex of the photo field effect transistor may be increased. Thus, since the amount of light passing through the light filter layer is increased, it may be confirmed that the photocurrent measured in the photo field effect transistor is increased.

Experimental Example 1

Figure 8A:
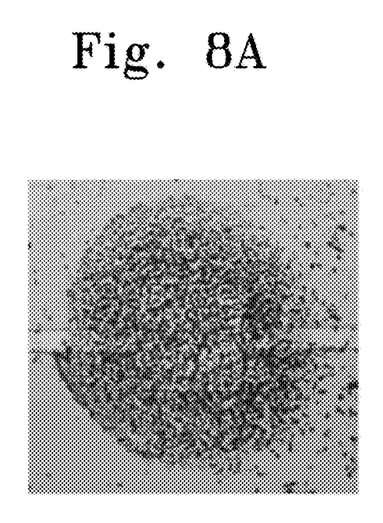
FIG. 8A is a photograph of a magnetic particle-multiprotein complex placed according to Experimental Example 1 of the present invention.

A photo field effect transistor having a horizontal length of about 100 μm and a vertical length of about 100 μm was prepared. In the same method as that described above, a magnetic particle-multiprotein complex 100 including a magnetic particle 10 coated with an EDC coating film 11, a primary capture antibody 12 bound to the magnetic particle 10, a beta-amyloid 13 bound to the primary capture antibody 12, a detection antibody 14 bound to the beta-amyloid, and a secondary capture antibody (or a fluorescent body) 15 was formed. About $4 \times 10^4$ complexes 100 were exactly induced around the channel pattern to form a circular single layer. A photograph of the formed single layer is illustrated in FIG.

Figure 8B:
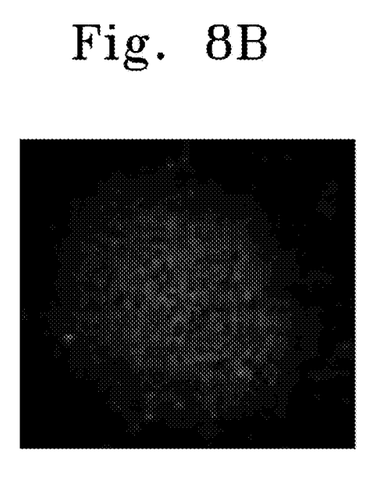
FIG. 8B is a photograph of light emitted by a fluorescent material when excitation beam is irradiated to a magnetic particle-multiprotein complex according to Experimental Example 1 of the present invention.

8A. In the state of FIG. 8A, excitation beam was irradiated to emit light from the fluorescent material, and a photograph of the emitted light was take and was illustrated in FIG. 8B. By doing so, it may be seen that the present invention could be realized.

Experimental Example 2

A photo field effect transistor that is the same as that in Experimental Example 1 was prepared. As in Experimental Example 1, magnetic particle-multiprotein complexes 100 were formed. At this time, four samples including beta-amyloids having different amounts were prepared. About $4 \times 10^4$ magnetic particle-multiprotein complexes 100 were placed on the channel pattern of the photo field effect transistor by using a magnet, photographs of the lights emitted by irradiating light were taken and illustrated in FIGS. 9A through 9D.

Figure 9A:
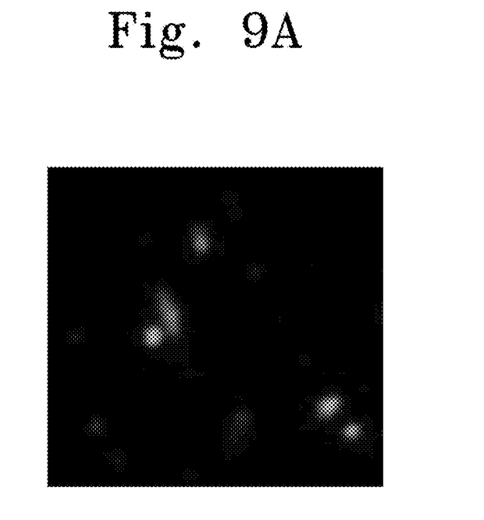
FIGS. 9A through 9D are photographs illustrating brightness of fluorescent light emitted when the amount of beta amyloid is changed according to Experimental Example 2 of the present invention.
Figure 9B:
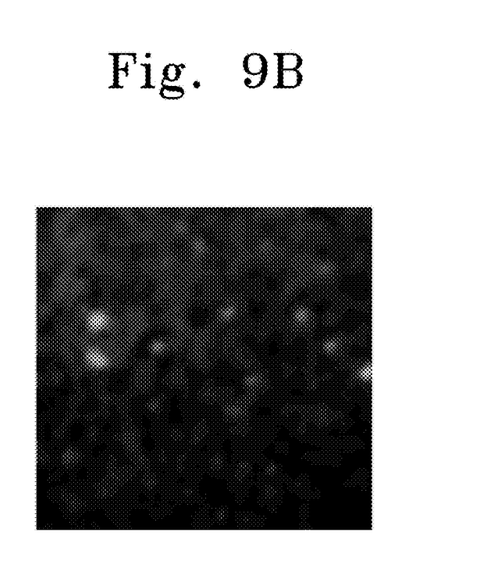
Figure 9C:
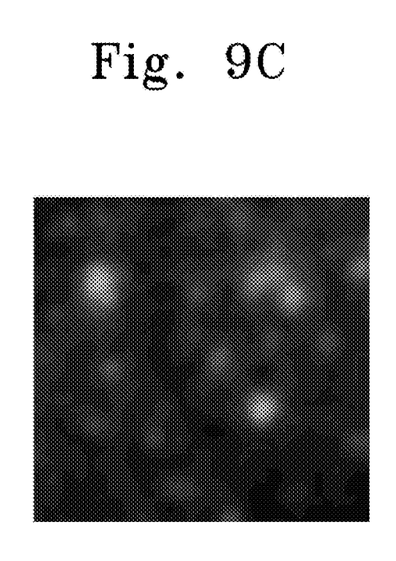
Figure 9D:
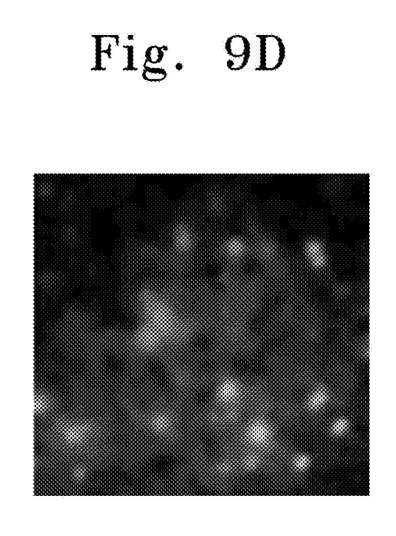

FIG. 9A is a photograph of the light emitted from a sample including the smallest amount of beta-amyloid, and FIGS. 9C through 9D are photographs of samples including beta-amyloid of which the amount is increased as it goes to FIG. 9D. Referring to FIGS. 9A through 9D, it may be seen that the brightness of the fluorescent light was increased as the amount of beta-amyloid is increased.

According to an embodiment of the present invention, it is possible to detect beta-amyloid protein from a biomaterial of a suspected Alzheimer's disease patient.

Alzheimer's disease may be simply diagnosed by disposing a magnetic particle-multiprotein complex reacted with the biomaterial in a photo field effect transistor and measuring a photocurrent generated due to a fine current. That is, whether a subject is an Alzheimer's disease patient or a normal person may be distinguishably diagnosed by quantitatively and exactly determining Alzheimer's disease according to the amount of beta-amyloid existing in the biomaterial.

Also, by grading Alzheimer's disease severity according to the change in photocurrent, early diagnosis and severity of Alzheimer's disease for a subject may be quantified.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A method for measuring a concentration of beta-amyloid in a sample, comprising:
    preparing magnetic particles on which primary capture antibodies specifically bound to beta-amyloid are adsorbed;
    decomposing a biomaterial including the beta-amyloid;
    binding the beta-amyloid to the primary capture antibodies;
    binding secondary capture antibodies labeled with a fluorescent material to the magnetic particles bound to the beta-amyloid to form a complex;
    disposing the complex over a channel pattern of a photo field effect transistor having a photocurrent that is changed according to an amount of incident light; and
    measuring the photocurrent changed by light excited from the complex to quantify the concentration of the beta-amyloid existing in the biomaterial,
    wherein the photo field effect transistor includes:
        a semiconductor substrate;
        an insulating layer disposed on the semiconductor substrate;
        the channel pattern, which is disposed on the insulating layer;
        first and second wiring electrodes disposed directly on an upper surface of the channel pattern, an upper surface of the insulating layer, and sidewalls of the channel pattern; and
        a light filter layer disposed on the upper surface of the channel pattern and sidewalls of the first and second wiring electrodes,
    wherein the channel pattern is defined by a side of the insulating layer and a side of the light filter layer, the first and second wiring electrodes defining sidewalls of the channel pattern,
    wherein disposing the complex comprises fixing the complex onto a surface of the light filter layer and over the channel pattern of the photo field effect transistor by a source of an external magnetic field located under the semiconductor substrate, and
    wherein the light filter layer passes through only a wavelength of light excited from the fluorescent material.

2. The method of claim 1, wherein the light filter layer is a selenium (Se) thin layer.

3. The method of claim 1, wherein the fluorescent material is formed of a material emitting light of a wavelength band ranging from about 650 nm to about 850 nm by excitation beam of a wavelength band ranging from about 400 nm to about 550 nm.

4. The method of claim 1, wherein the magnetic particles comprise at least one of Fe, Mn, Ni, and Co.

5. The method of claim 1, wherein the magnetic particles have a diameter ranging from about 100 nm to about 5 μm.

6. The method of claim 1, wherein the primary capture antibodies are bound to the magnetic particles by a chemical reaction of EDC (1-ethyl-3-(3-dimethylaminopropyl) carbodiimide) or CMC (1-cyclohexyl-3(2-morpholinoethyl) carbodiimide metho-p toluensulfonate).

7. The method of claim 1, wherein the primary capture antibody is a monoclonal antibody, and the secondary capture antibody is a polyclonal antibody.

8. The method of claim 1, further binding blocking molecules to surfaces of the magnetic particles on which the primary capture antibodies are not bound.

9. The method of claim 1, wherein the primary capture antibody is adsorbed by a carboxyl group (—COOH), a thiol group (—SH), a hydroxyl group (—OH), a silane group, an amine group (—NH2) or an epoxy group which is induced to surfaces of the magnetic particles.

10. The method of claim 1, wherein the biomaterial is at least one of spinal fluid, blood and olfactory cell.

11. The method of claim 1, wherein the source of the external magnetic field is a small sized magnet or a magnetic field generating unit.

12. The method of claim 1,
    wherein the photo field effect transistor has a length of 100 μm and a width of 100 μm, and
    wherein the complexes are fixed on the channel pattern in a single layer.

* * * * *